United States Patent
Buurman

[19]

[11] Patent Number: 5,902,239
[45] Date of Patent: *May 11, 1999

[54] IMAGE GUIDED SURGERY SYSTEM INCLUDING A UNIT FOR TRANSFORMING PATIENT POSITIONS TO IMAGE POSITIONS

[75] Inventor: Johannes Buurman, Eindhoven, Netherlands

[73] Assignee: U.S. Philips Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/739,763

[22] Filed: Oct. 30, 1996

[51] Int. Cl.$^6$ .................................................... A61B 5/00
[52] U.S. Cl. ..................... 600/427; 600/429; 606/130
[58] Field of Search ..................... 128/653.1; 606/130; 600/427, 426, 429, 414, 417

[56] References Cited

U.S. PATENT DOCUMENTS 5,186,174  2/1993  Schlondorff et al. .................... 600/429
5,243,984  9/1993  Ogura et al. ........................... 128/653.1
5,309,913  5/1994  Kormos et al. ........................ 128/653.1

OTHER PUBLICATIONS

"An Automatic Registration Method For Frameless Stereotaxy, Image Guided Surgery, And Enhanced Reality Visualization", W.E.L. Grimson, IEEE Transactions On Medical Imaging, vol. 15, No. 2, Apr. 1996.

*Primary Examiner*—Ruth S. Smith
*Attorney, Agent, or Firm*—Dwight H. Renfrew, Jr.

[57] ABSTRACT

An image guided surgery system includes a position detection system which has a camera unit (1) and which measures positions of markers on the patient (12) and of a surgical instrument (11). The image guided surgery system also includes a transformation unit (30) which automatically derives the mapping associated with imaging of the patient. The imaging is for example performed by way of x-ray computed tomography or magnetic resonance imaging. The transformation unit (30) is arranged to match positions on the patient (12) to positions in the image. To that end the transformation unit computes the minimum of a cost function.

12 Claims, 1 Drawing Sheet

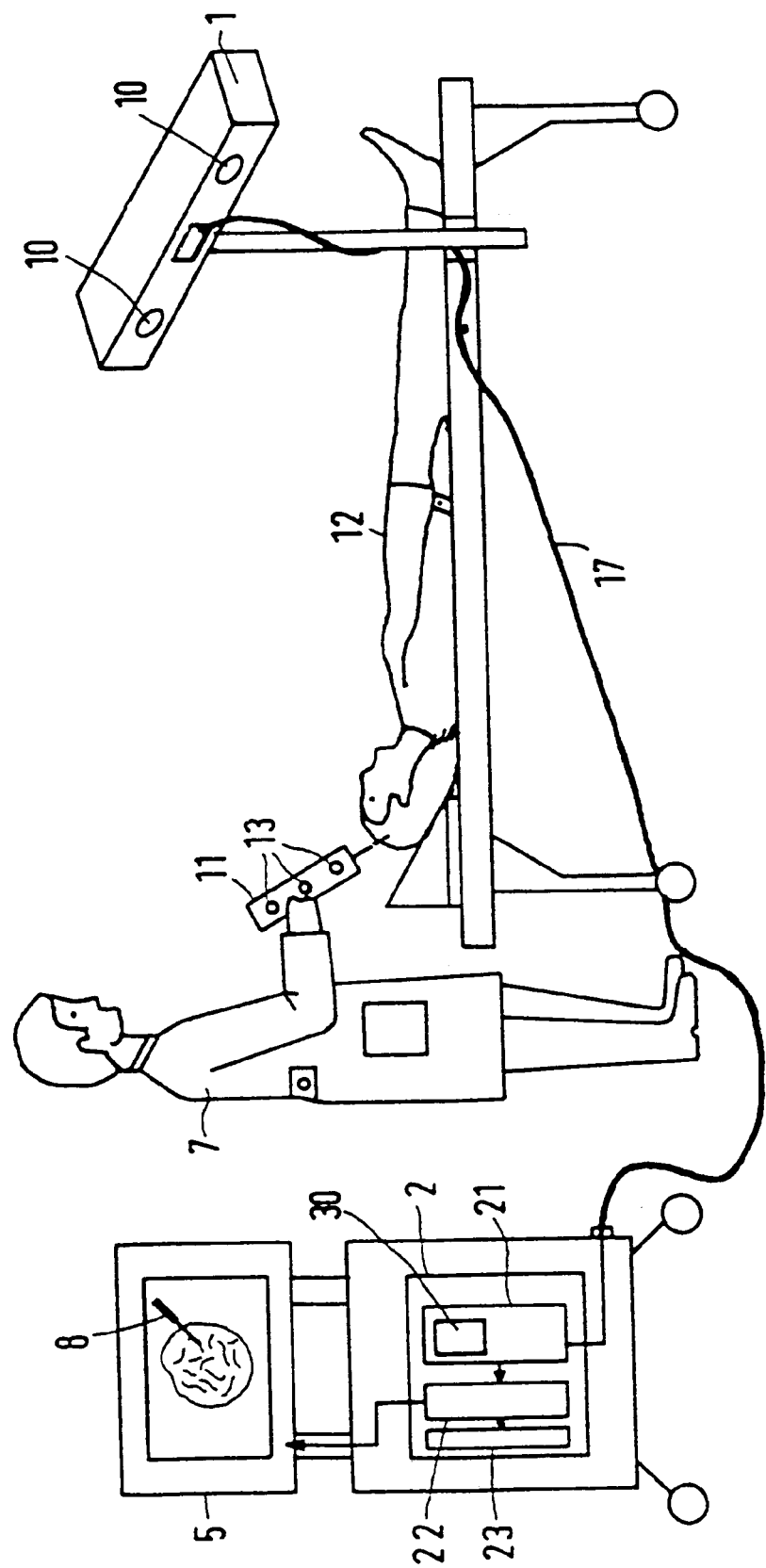

IMAGE GUIDED SURGERY SYSTEM INCLUDING A UNIT FOR TRANSFORMING PATIENT POSITIONS TO IMAGE POSITIONS

BACKGROUND OF THE INVENTION

1. Field of the Invention

The invention relates to an image-guided surgery system including a position detection system and a transformation unit.

2. Description of the Related Art

Such an image-guided surgery system is known from U.S. Pat. No. 5,186,174.

During complicated surgery it is often very difficult or even impossible for a surgeon to see directly where in the interior of a patient he/she moves a surgical instrument. Surgery may be aimed at a therapeutic goal, e.g. to remove malignant tissue, or surgery may be aimed at a diagnostic goal e.g. to examine the interior of a patient's anatomy. Surgery includes various methods of entering a patient's body with a surgical instrument. An image guided surgery systems shows the surgeon a position of a surgical instrument in an operating region in the body of a patient during a surgical operation. Before or during the operation images, such as x-ray computed tomography or magnetic resonance images of the patient are formed. During the operation a position detection system measures the position of the surgical instrument relative to the patient and a computer calculates the position in the relevant image which corresponds to the position of the surgical instrument. On a display device the image guided surgery system displays such an e.g. CT or MRI image in which also the actual position of the surgical instrument is indicated. Thus, although the instrument is beyond direct sight to the surgeon, the image guided surgery system enables the surgeon to see where the surgical instrument is inside the patient. The surgeon is thus also able to see how the surgical instrument can be moved in the patient without risk of damaging vital parts.

The position detection system of the known image guided surgery system comprises an articulated arm with potentiometers at its joints for measuring the orientation of the arm. The position detection system includes a data processor for deriving the position in space of the surgical instrument from the signals from the potentiometers.

In the image fiducial markers are imaged which are placed on particular positions on the patient. For example in neurosurgery lead or MR susceptible markers are placed in the area of the patient's head to be operated on. At the start of the operation the fiducial markers are indicated with the surgical instrument or with a separate pointing device and the positions in space of the fiducial markers are measured by the position detection system. For respective markers, their corresponding images of markers in the earlier generated image are also indicated. The data processor calculates the transformation matrix which associates the positions in space of the fiducial markers with the corresponding positions of the images of the markers in the earlier generated image. This transformation matrix is subsequently used to compute a corresponding position in the image for a position in space in the actual operating region.

The article *An automatic registration method for frameless stereotaxy, image-guided surgery, and enhanced reality visualization*, in IEEE transactions on medical imaging 15(1996)129 by W. E. L. Grimson et al. discloses a transformation which maps a set of measured positions to a surface in segmented MRI data. The method disclosed therein starts from a huge number of hypothetical transformations which map sets of points on the patient to sets of points in the MRI image.

SUMMARY OF THE INVENTION

An object of the invention is to provide an image-guided surgery system with which it is easier to derive a transformation which maps positions on the patient on positions in the image.

This object is achieved by the image-guided surgery system according to the invention which is characterized in that the transformer unit is arranged to automatically match a set of positions on a patient to a set of positions in an image.

The image guided surgery system comprises a position detection system which measures positions in space of the markers on the patient and of the surgical instrument. Preferably, an optical position detection system is employed which comprises one or several cameras for imaging the patient with the markers and the surgical instrument from several orientations. The markers can be fiducial markers, but particular features of the patient's anatomy which are recognizable in the image are also suitable as markers. The transformation unit is set up or configured to calculate the mapping associated with the imaging of the patient from the positions of the markers on the patient and the corresponding positions of the images of the markers in the image. According to this mapping to any position in or on the part of the patient which is imaged there can be assigned the corresponding position in the image.

Matching of positions on the patient to positions in the image is in effect the formation of pairs, each pair consisting of a position on the patient and a position in the image such that within each pair the position in the image relates to the image of a marker at the position on the patient. In fact the matching forms pairs of positions that are corresponding according to the imaging that was performed earlier, such as CT or MRI imaging of the patient. The image-guided surgery system according to the invention does not require that the matching pairs of the positions of the fiducial markers on the patient and the positions in the image representing said fiducial markers are separately and/or manually determined. In particular, there is no need to assign the same order of succession in which measured positions of the fiducial markers on the patient are indicated and in which the corresponding positions in the image are indicated. Hence, operation of the image-guided surgery system according to the invention is less complicated as compared to the conventional image-guided surgery system. Because the markers on the patient and their images may be indicated in a random order, the indication of the marker positions and their images requires only very little time, such as a few seconds. Moreover, the image-guided surgery system according to the invention is far less susceptible to errors in the indication of the markers and their images because the image-guided surgery system according to the invention arrives at the correct transformation irrespective of the order in which the markers on the patient and their images are indicated. Thus, it is avoided that the initialization of the position detection system must be repeated because an error was made.

A preferred embodiment of an image-guided surgery system according to the invention is characterized in that the transformer unit incorporates an arithmetic unit arranged to optimize a cost function which depends on distances between respective transformed positions in space located on the patient on the patient and corresponding positions in the image.

Optimizing the cost function includes determining an extremum, i.e. maximum or minimum value for a number of possible pairings or a matching of positions of markers on the patient and positions of their images. Whether a minimum or a maximum value is to be determined depends on the precise form of the cost function that is employed. In practice very good results are obtained with a cost function that depends on the sum of the squared distances between positions in the image of mapped markers on the patient and the positions in the image of the image of the markers. Each mapping is defined by indicating pairs of positions of markers on the patient and positions of their images. Only rigid mappings, i.e. mappings including only translations and rotations are considered. The mapping that corresponds to the minimum value of the cost function then optimally maps markers on the patient onto the positions of their images in a least squares sense. This mapping accurately represents the transformation from positions of markers on the patient to positions of their images in the image.

A further preferred embodiment of the image-guided surgery system according to the invention is characterized in that the arithmetic unit is arranged to reduce influence of erroneous points on the optimizing of the cost function.

Erroneous positions are positions on the patient and/or positions in the image which cannot be matched. In practice such erroneous positions may occur because a position outside the region of the patient which is imaged, or even outside the patient at all, is indicated. Another cause of an erroneous position is an indication of a position in the image which does not relate to an imaged part of the patient. Thus, a pair of positions one of which is erroneous cannot be matched and is therefore denoted an unmatched pair. A pair of positions is considered to be unmatched when such a pair would yield a contribution to the cost function exceeding a predetermined threshold if the pair were considered as a pair that is associated with a rigid mapping. Because the influence of such erroneous points on the automatic matching is reduced hardly any computational effort is wasted in trying to find a mapping which attempts to match positions that cannot be matched at all. Preferably, a relatively high contribution to the cost function is assigned to an unmatched pair, so as to reduce the influence of erroneous positions. In particular, the contribution to the cost function of an unmatched pair is multiplied by a predetermined factor relative to a contribution of a matched pair; preferably the predetermined factor relates to the square of a predetermined maximum distance between two positions which is still acceptable as a matched pair.

A further preferred embodiment of the image-guided surgery system according to the invention is characterized in that the transformation unit is arranged to select small subsets of positions on the patient and small corresponding subsets of positions in the image for obtaining an accurate initial estimate for the transformation.

A further preferred embodiment of the image-guided surgery system according to the invention is characterized in that said subsets are triplets.

In order to avoid calculations that relate to a large number pairs of positions in the image and on the patient which are improbable to form a matched pair an initial estimate is based on a small subset of pairs of positions on the patient and positions in the image. It appears that a rather accurate initial estimate for the matching is obtained. Consequently very little computation time is required to derive an accurate matching for all markers starting from that initial estimate. Preferably, the subsets on which the initial estimate is based are chosen heuristically such that respective geometries of subsets of positions on the patient correspond to geometries of subsets of positions in the image. In this respect it is advantageous to choose subsets of positions on the patient and in the image respectively which comprise subsets which have a similar shape and of which comprise positions that are far apart. In practice it appears that it is convenient as to required computational power and computation time to choose triplets of positions in the image and on the patient respectively as subsets in order to obtain the initial estimate.

Further it is noted that the functions of the transformation unit of the image-guided surgery system according to the invention can be performed by means of a suitably programmed computer or by a special purpose processor that incorporates circuitry designed to perform the steps of the image-guided surgery system according to the invention. An image guided surgery system according to the invention preferably incorporates such a suitably programmed computer or special purpose processor.

BRIEF DESCRIPTION OF THE DRAWINGS

These and other aspects of the invention are elucidated with respect to the embodiments discussed hereinafter and with reference to the accompanying drawing wherein:

The FIGURE shows a schematic diagram of an image guided surgery system according to the invention.

DESCRIPTION OF THE PREFERRED EMBODIMENTS

Referring to the sole FIGURE, the image guided surgery system comprises a position detection system 1, 2 which includes a camera unit 1 with one or more cameras 10 and a data processor 2. The one or several cameras pick-up images from different directions of a surgical instrument 11. The surgical instrument is manipulated by a surgeon 7 during the surgical procedure. For example, the camera unit 1 incorporates two CCD image sensors mounted on a rigid frame. The frame is moveable so as to direct the CCD sensors to the operating region. The image signals from separate cameras, or subsequent image signals from the single camera but from successive camera positions are supplied to the data processor 2. To that end the camera unit 1 is coupled to the data processor 2 by way of a cable 17. The data processor 2 includes a computer 21 which, on the basis of the image signals, computes the position of the surgical instrument relative to the patient 12 who is undergoing a surgical operation. The image processor 22 is incorporated in the data processor 2. The surgical instrument is fitted with light or infrared emitting diodes 13 (LEDs or IREDs) which emit radiation to which the cameras 10 are sensitive. The computer 21 also computes the corresponding position of the surgical instrument 11 in an earlier generated image such as a CT image or an MRI image. The CT data and/or MRI data are stored in a memory unit 23. The computer 21 may be alternatively programmed to calculate the coordinates of the position of the surgical instrument with respect to a fixed reference system, then the image processor 22 is arranged to convert those coordinates to the corresponding position in the image.

In the image data fiducial markers are imaged which are placed on particular positions on the patient. For example lead or MR susceptible markers are placed at the temples, behind the ears, on shaved parts of the skull and on the forehead of the patient. At the start of the operation the fiducial markers are indicated with a surgical instrument and their positions in space are measured by the position detection system. The computer 21 calculates the transformation matrix which mathematically connects the positions in space of the fiducial markers to the corresponding positions of the images of the markers in the earlier generated image. This transformation matrix is subsequently used to compute a corresponding position in the image for a position in space in the actual operating region. According to the invention, the image guided surgery system is provided with a transformation unit 30 which automatically derives the transformation corresponding to the imaging from the marker positions and their images. The transformation unit 30 receives position data of the markers on the patient 12 when the markers are indicated on the patient. The transformation unit 30 also receives position data of the positions of the images of those markers in the image; to this end the images of the markers are indicated on a rendition of the image. The transformer unit 30 computes the rigid mapping which corresponds with the imaging irrespective of the order in which positions on the patient and in the image are indicated. From pairs respective positions on the patient and in the image a rigid mapping which contains at most a rotation and a translation is derived which best matches the pairs at issue. For that rigid mapping the cost function is computed which is in fact a measure of the accuracy of the mapping. That is the preferred cost function for the method according to the invention is $$C(M) = \sum_i \{d[M(p_i), q_i)]^2\} + Nd_{max}^2$$

where $p_1$ are positions on the patient, $q_1$ are positions in the image and M is a rigid mapping which maps positions on the patient in the operating theater to positions in the image of the patient. The maximum distance of a position $q_1$ in the image and associated mapped position $M(p_1)$ that is taken into account is $d_{max}$. If the distance is larger, then the position at issue it considered erroneous and is part of an unmatched pair. The total number of unmatched pairs is denoted N. The contribution $Nd_{max}^2$ to the cost function reduces the influence of erroneous positions on the search for the best mapping without the need for much computation effort. The rigid mapping $\overline{M}$ which substantially corresponds to the mapping associated with the imaging of the patient satisfies $$C\overline{M}=\min_M[C(M)]$$

The minimization is carried out over all rigid mappings M which are defined by assigning positions in the image as mappings of positions on the patient.

The computation of the cost function is performed by means of an arithmetic unit which is preferably incorporated in the computer 21. The mapping which minimizes the cost function is selected as the mapping which accurately corresponds with the imaging. According to the selected mapping any position in or on the patient is transformed into a corresponding position in the image. In particular, from the position of the surgical instrument which is measured by the optical position detection system the corresponding position in the image is computed according the mapping which minimizes the cost function. Because it is not required to indicate the positions on the patient and in the image is a special order, the indication of the positions takes only a short period of time. It appears that in practice the indication of the positions can be done within 2 to 5 seconds.

As has been mentioned, it is advantageous to choose subsets of positions on the patient and in the image respectively which comprise subsets which have a similar shape and of which comprise positions that are far apart and in practice it appears that it is convenient as to required computational power and computation time concerned to chose triplets of positions in the image and on the patient respectively as subsets in order to obtain the initial estimate. For eight markers typically fifty triplets are tried which requires about 100 us to 1 ms of computing time. Preferably triplets of points on the patient and in the image respectively are chosen which form respective triangles having approximately the same shape. Moreover, it turns out that a particularly good estimate is rapidly obtained from triangles having vertices which are far apart. A modern workstation, like a Sun SPARCStation 5 operating at 110 MHz, requires about 100 ms of computing time for computing the overall matching based on all marker positions.

The data from the memory unit are supplied to the image processor. The position-data computed by the computer 21 are also supplied to the image processor 22. The image processor is further arranged to select an appropriate set of image data on the basis of the position of the surgical instrument. Such an appropriate set e.g. represents CT or MRI image data of a particular slice through the operating region. The image processor 22 generates an image signal which combines the earlier generated image data with the corresponding position of the surgical instrument. In a rendition of the earlier generated image information, also the corresponding position 8 of the surgical instrument is shown. The real-time image showing the position of the surgical instrument in the operating region is displayed on the display device 5. The display device is e.g. a monitor comprising a cathode-ray tube, but an LCD display screen may be used as well.

I claim:

1. A system for displaying the position of a surgical instrument in an operating region of a patient comprising:

a position detection system for measuring spatial positions in the operating region of a patient, a memory unit for storing an image of the operating region of the patient, transformation means for (i) providing a matching of measurements of spatial positions in the operating region recognizable in the image of the operating region with measurements of image positions recognizable in the image of the operating region by selecting matched pairs of a spatial position measurement with a corresponding image position measurement, wherein the spatial measurements and the image measurements are unordered with respect to each other, and wherein said selecting matched pairs optimizes a cost function that depends on possible matchings of spatial positions with image positions so that said transformation means provides a matching that optimizes said cost function, and (ii) determining from the matched pairs of the provided matching a rigid mapping of spatial positions in the operating region to image positions in the image of the operating region, a computer programmed to map according to said rigid mapping a spatial position of the surgical instrument measured by said position detection system to an image position in the image of the operating region, and a display for displaying the mapped image position of the surgical instrument superimposed on the image of the operating region retrieved from said memory unit.

2. The system of claim 1 wherein said transformation means comprise a computer programmed to provide a matching and to determine a rigid mapping.

3. The system of claim 1 wherein said transformation means comprise a special purpose processor incorporating circuitry to provide a matching and to determine a rigid mapping.

4. The system of claim 1 wherein the rigid mapping comprises a transformation matrix, wherein said transformation means determines the transformation matrix from the matched pairs of the provided matching, and wherein said programmed computer applies the transformation matrix to a spatial position measurement.

5. The system of claim 1 wherein the spatial position measurements are measured by said position detection system separately from and in an order independent of the measurements of the image positions in the image.

6. The system of claim 1 wherein said transformation means provides from a plurality of matchings a matching for which the cost function has an optimum value.

7. The system of claim 1 wherein said transformation means determines the value of said cost function for each possible matching from differences between the image position measurement of each matched pair of a possible matching and the image position mapped from the spatial position measurement of each matched pair according to a rigid mapping determined by the possible matching.

8. The system of claim 7 wherein the value of the cost function is determined from a sum of squares of distances between the image position measurement of each matched pair and the image position mapped from the spatial position measurement of that matched pair.

9. The system of claim 1 wherein an erroneous position in a possible matching is an image position measurement or a spatial position measurement that occurs in a matched pair of that possible matching and that has a contribution to the cost function exceeding a predetermined threshold, and wherein said transformation means reduces the contribution of an erroneous position to said cost function.

10. The system of claim 9 wherein the contribution of an erroneous position is reduced by assigning it a fixed value.

11. The system of claim 1 wherein said transformation means further comprises means for performing an initial matching depending on only a subset of the spatial position measurements and on only a subset of the image position measurements.

12. The system of claim 11 wherein the size of the subset of spatial position measurements is three, and the size of the subset of image position measurements is three.

* * * * *